(12) United States Patent
Mou et al.

(10) Patent No.: US 10,773,017 B2
(45) Date of Patent: Sep. 15, 2020

(54) MICRO PUMP

(71) Applicant: Microjet Technology Co., Ltd., Hsinchu (TW)

(72) Inventors: Hao-Jan Mou, Hsinchu (TW); Li-Pang Mo, Hsinchu (TW); Yung-Lung Han, Hsinchu (TW); Chi-Feng Huang, Hsinchu (TW); Chang-Yen Tsai, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 162 days.

(21) Appl. No.: 16/124,751

(22) Filed: Sep. 7, 2018

(65) Prior Publication Data

US 2019/0125965 A1 May 2, 2019

(30) Foreign Application Priority Data

Oct. 27, 2017 (TW) .............................. 106137199 A

(51) Int. Cl.
*A61M 5/14* (2006.01)
*A61M 5/142* (2006.01)
(Continued)

(52) U.S. Cl.
CPC ........... *A61M 5/14276* (2013.01); *B82Y 5/00* (2013.01); *F04B 43/043* (2013.01);
(Continued)

(58) Field of Classification Search
CPC ....... A61M 5/14276; A61M 2205/0244; F04B 43/043; F04B 53/1072; F04B 43/046;
(Continued)

(56) References Cited

U.S. PATENT DOCUMENTS 6,261,066 B1 7/2001 Linnemann et al.
2004/0120836 A1 6/2004 Dai et al.
(Continued)

FOREIGN PATENT DOCUMENTS

CN 103237492 A 8/2013
EP 3203078 A1 8/2017
(Continued)

OTHER PUBLICATIONS

Extended European Search Report for European Application No. 18193124.7, dated Mar. 8, 2019.

*Primary Examiner* — Amber R Stiles
(74) *Attorney, Agent, or Firm* — Birch, Stewart, Kolasch & Birch, LLP

(57) ABSTRACT

A micro pump is applied to be implanted into human's blood vessels and includes a substrate, a flow-guiding-and-actuating unit, plural switching valves, a driving chip and a micro-monitor. The substrate has plural guiding channels including an inlet channel, an outlet channel and a branch channel. The flow-guiding-and-actuating unit covers a compressing chamber, and is enabled to change the volume of the compressing chamber so as to transport fluid. When a communication connector of the driving chip receives an external command, the driving chip enables the flow-guiding-and-actuating unit and the micro-monitor, and controls the open/closed states of the switching valves covering an outlet aperture and a storage outlet, thereby the flow-guiding-and-actuating unit drives the fluid medicine from a storage chamber to the outlet aperture, so as to deliver the fluid medicine to a target blood vessel.

17 Claims, 11 Drawing Sheets

(51) Int. Cl.
*F04B 43/04* (2006.01)
*F04B 53/10* (2006.01)
*B82Y 5/00* (2011.01)
*A61B 17/00* (2006.01)

(52) U.S. Cl.
CPC ........ *F04B 43/046* (2013.01); *F04B 53/1072* (2013.01); *A61B 2017/00022* (2013.01); *A61B 2017/00345* (2013.01); *A61B 2562/028* (2013.01); *A61M 2205/0244* (2013.01)

(58) Field of Classification Search
CPC ............ B82Y 5/00; A61B 2017/00022; A61B 2017/00345; A61B 2562/028
See application file for complete search history.

(56) References Cited

U.S. PATENT DOCUMENTS

2008/0107739 A1* 5/2008 Kraft ................ A61M 5/14276
424/489
2011/0293489 A1 12/2011 Zhou et al.

FOREIGN PATENT DOCUMENTS

| TW | 200942332 | A | 10/2009 |
| TW | 201514379 | A | 4/2015 |

\* cited by examiner

US 10,773,017 B2

MICRO PUMP

FIELD OF THE INVENTION

The present disclosure relates to a micro pump, and more particularly to a miniature, thin and silent micro pump.

BACKGROUND OF THE INVENTION

In the current situation, the patients take medicine regularly or when they feel uncomfortable in their bodies. When the patients take the medicine, the medicine must be delivered into the patients' body or blood vessel by oral or injection. The patient must carry a therapeutic drug or an injection tool anytime and anywhere. While in a case of missing a drug treatment, it may cause irreparable harm to the patient. In addition, since the patient must carry the therapeutic drug or the injection tool anytime and anywhere, it is very inconvenient in life or to go out.

Therefore, there is a need of providing a micro pump to address the above-mentioned issues in prior arts. By utilizing the micro pump, it benefits to meet the requirement of detecting the physical condition of the patient at anytime and anywhere and immediately delivering the therapeutic drug into the human blood.

SUMMARY OF THE INVENTION

The object of the present disclosure is to provide a micro pump, which is produced by a nanometer process and can be implanted into human blood vessels, to overcome the current situations that the prior art fails to detect the human body condition at anytime and anywhere and fails to immediately deliver the therapeutic drug.

In accordance with an aspect of the present disclosure, a micro pump applied to be implanted in human blood is provided. The micro pump includes a substrate, a guiding actuation unit, a plurality of switching valves, a driving chip and a micro-monitor. The substrate includes a plurality of guiding channels produced by a nanometer process, a compressing chamber and a storage chamber, a first covering component and a second covering component. The plurality of guiding channels includes an inlet channel, an outlet channel and a branch channel in communication with the inlet channel. The first covering component covers the inlet channel, the outlet channel and the branch channel and includes an inlet aperture corresponding to the inlet channel and an outlet aperture corresponding to the outlet channel. The compressing chamber is in communication with the inlet channel and the outlet channel. The second covering component covers the storage chamber so as to store a medicine fluid in the storage chamber. The storage chamber has a storage outlet in communication with the branch channel. The flow-guiding-and-actuating unit is produced by the nanometer process and configured to cover the compressing chamber, wherein in response to an applied power, the flow-guiding-and-actuating unit is actuated to change the volume of the compressing chamber so as to transport fluid. The plurality of switching valves are produced by the nanometer process and cover the inlet aperture, the outlet aperture and the storage outlet, respectively. The driving chip is produced by the nanometer process and packaged on the substrate in a system-in-package manner so as to provide the flow-guiding-and-actuating unit with the power and control the flow-guiding-and-actuating unit to actuate. The plurality of switching valves are controlled to be operated in an open or closed state, and the driving chip includes a communication connector. The micro-monitor is produced by the nanometer process, packaged on the substrate in a system-in-package manner, and enabled by the driving chip. The micro pump is implanted in a human blood vessel and receives an external command through the communication connector of the driving chip. The driving chip controls the flow-guiding-and-actuating unit and the micro-monitor to be enabled, and controls the open/closed states of the switching valves covering the inlet aperture and the outlet aperture, so that a fluid flow is generated. The kinetic energy that the fluid flow possesses facilitates displacement of the micro pump in the blood vessel. Meanwhile, the enabled micro-monitor keeps monitoring for positioning a target blood vessel needing to be treated. While the switching valve corresponding to the inlet aperture is closed and the switching valves corresponding to the outlet aperture and the storage outlet are opened, the medicine fluid stored in the storage chamber is transported to the outlet aperture by the flow-guiding-and-actuating unit and delivered to the target blood vessel.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

Figure 1:
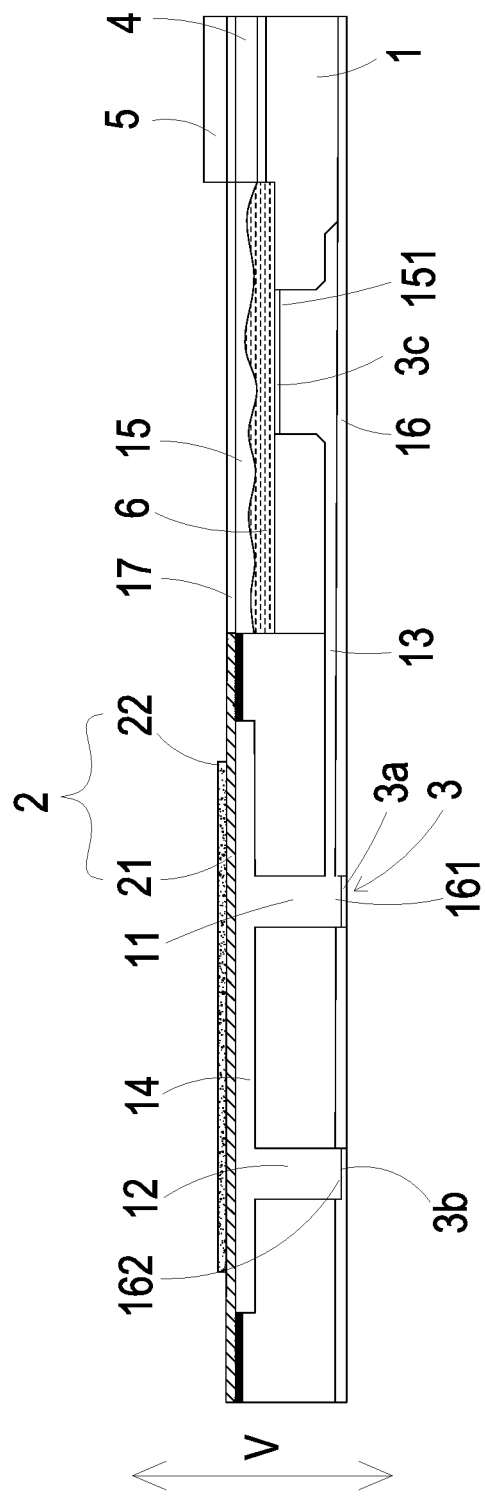
FIG. 1 is a cross sectional view illustrating a micro pump according to a first embodiment of the present disclosure.

The present disclosure will now be described more specifically with reference to the following embodiments. It should be noted that the following descriptions of preferred embodiments of this disclosure are presented herein for purpose of illustration and description only. It is not intended to be exhaustive or to be limited to the precise form disclosed.

The present disclosure provides a micro pump including at least one substrate 1, a plurality of guiding channels, at least one compressing chamber 14, at least one storage chamber 15, at least one inlet channel 11, at least one outlet channel 12, at least one branch channel 13, at least one first covering component 16, at least one inlet aperture 161, at least one outlet aperture 162, at least one second covering component 17, at least one medicine fluid 6, at least one storage outlet 151, at least one flow-guiding-and-actuating unit 2, a plurality of switching valve 3/3a/3b/3c, at least one driving chip 4, at least one communication connector and at least one micro-monitor 5. The numbers of the substrate 1, the compressing chamber 14, the storage chamber 15, the inlet channel 11, the outlet channel2, the branch channel 13, the first covering component 16, the inlet aperture 161, the outlet aperture 162, the second covering component 17, the medicine fluid 6, the storage outlet 151, the flow-guiding-and-actuating unit 2, the driving chip 4, the communication connector and the micro-monitor 5 are exemplified by one for each respectively in the following embodiments but not limited thereto. It is noted that each of the substrate 1, the compressing chamber 14, the storage chamber 15, the inlet channel 11, the outlet channel2, the branch channel 13, the first covering component 16, the inlet aperture 161, the outlet aperture 162, the second covering component 17, the medicine fluid 6, the storage outlet 151, the flow-guiding-and-actuating unit 2, the driving chip 4, the communication connector and the micro-monitor 5 can also be provided in plural numbers.

The micro pump of the present invention is applied to be implanted into human blood to detect the health state of the patient and immediately deliver the therapeutic drug. Referring to FIG. 1, in the first embodiment of the present disclosure, the micro pump includes a substrate 1, a flow-guiding-and-actuating unit 2, a plurality of switching valves 3, a driving chip 4 and a micro-monitor 5. In this embodiment, the substrate 1, the flow-guiding-and-actuating unit 2, the switching valves 3, the driving chip 4 and the micro-monitor 5 are all produced by a nanometer process technology.

The substrate 1 comprises a plurality of flow guiding channels produced by a nanometer process, which include an inlet channel 11, an outlet channel 12 and a branch channel 13. The branch channel 13 is in communication with the inlet channel 11. The substrate 1 includes a first covering component 16 configured to cover an inlet aperture 161 of the inlet channel 11, an outlet aperture 162 of the outlet channel 12 and the branch channel 13. The substrate 1 further includes a compressing chamber 14 and a storage chamber 15 concavely formed on a surface thereof. The compressing chamber 14 is in communication with the inlet channel 11 and the outlet channel 12. The substrate 1 includes a second covering component 17 configured to cover the storage chamber 15 to form a space therein for storing the medicine fluid 6. Moreover, the storage chamber 15 has a storage outlet 151 in communication with the branch channel 13. The plurality of switching valves 3 include a switching valve 3a disposed in and covering the inlet aperture 161, a switching valve 3b disposed in and covering the outlet aperture 162, and a switching valve 3c disposed in and covering the storage outlet 151.

Please refer to FIG. 1 again. The flow-guiding-and-actuating unit 2 is configured to cover the compressing chamber 14, and includes a carrier 21 and an actuator 22. The actuator 22 can be for example but not limited to a piezoelectric component. The carrier 21 covers the compressing chamber 14 and the actuator 22 is attached to a surface of the carrier 21. The actuator 22 further includes a positive electrode (not shown) and negative electrode (not shown) in electrical connection with the driving chip 4. The actuator 22 is deformed when a voltage is applied thereon, so as to drive the carrier 21 to vibrate in a vertical direction (V) in a reciprocating manner. Thus, the volume of the compressing chamber 14 is compressed to make a change of the pressure in the compressing chamber 14 for transporting the fluid. The driving chip 4 is packaged on the substrate 1 in a system-in-package manner. The driving chip 4 powers and controls the flow-guiding-and-actuating unit 2. The driving chip 4 also controls the plurality of switching valves 3 to be operated in an open or closed state. The driving chip 4 includes a communication connector (not shown) for receiving an external command. The communication connector can transmit and receive information in a wireless communication manner or by a Bluetooth technology, but not limited thereto. In this embodiment, the driving chip 4 further includes a graphene battery (not shown) in electrical connection with the positive electrode (not shown) and the negative electrode (not shown) of the actuator 22 of the flow-guiding-and-actuating unit 2 for providing driving power. The micro-monitor 5 is packaged on the substrate 1 in a system-in-package manner and is controlled and enabled by the driving chip 4.

Figure 2A:
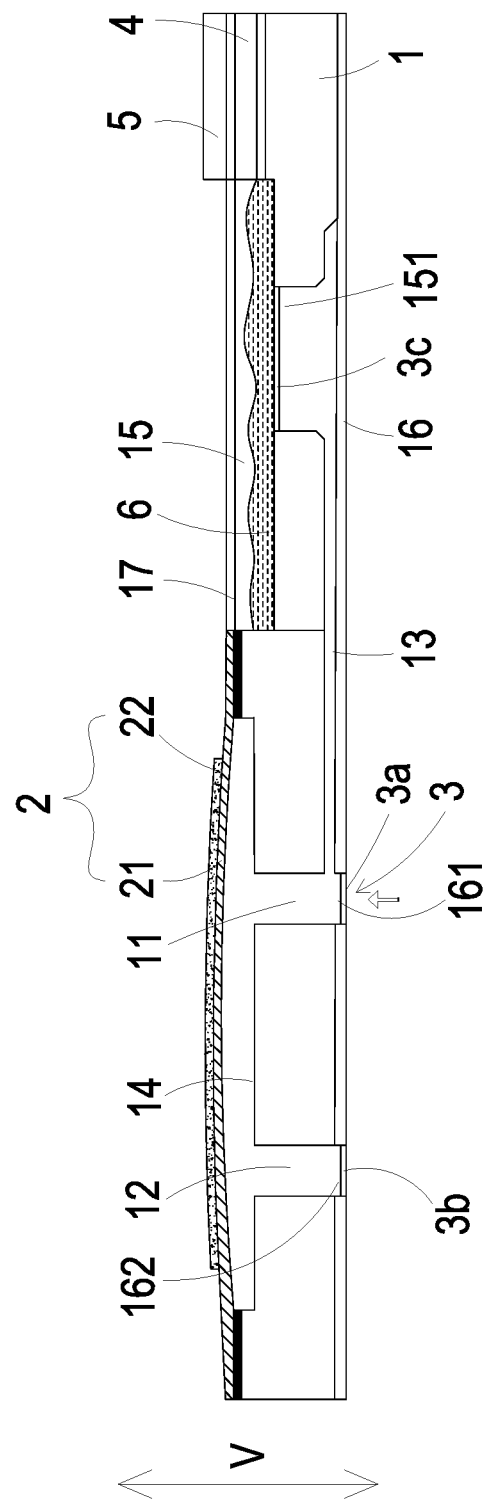
FIGS. 2A to 2D show actions of fluid in the micro pump of FIG. 1.
Figure 2B:
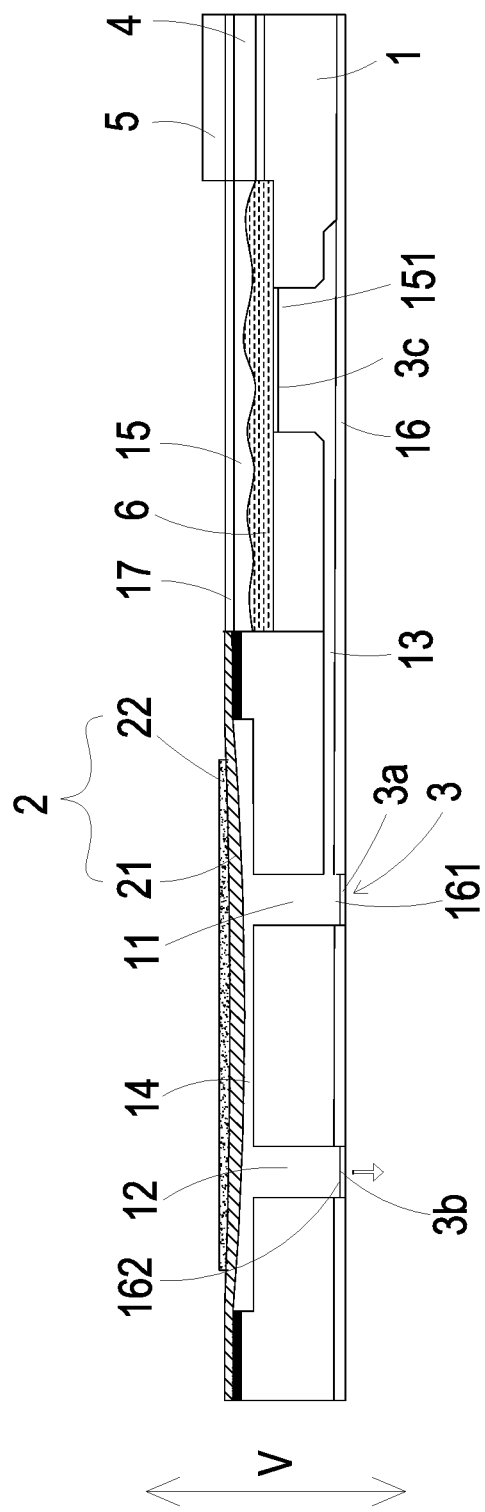

Please refer to FIGS. 2A and 2B. Firstly, the micro pump is implanted into a patient's blood vessel and receives an external command through the communication connector of the driving chip 4. In response to the external command received by the communication connector, the driving chip 4 controls the flow-guiding-and-actuating unit 2 and the micro-monitor 5 to be enabled. At the same time, the closed/open states of the switching valve 3a disposed in the inlet aperture 161 and the switching valve 3b disposed in the outlet aperture 162 are under control of the driving chip 4 (i.e., the switching valve 3a, 3b are alternatively opened), so as to make fluid (i.e., blood) flow as indicated by the arrows in the FIGS. 2A and 2B. Meanwhile, the kinetic energy that the flow of the fluid possesses can facilitate displacement of the micro pump in the blood vessel. During the motion of the micro pump, the micro-monitor 5 keeps monitoring to position a target blood vessel needing to be treated.

Figure 2C:
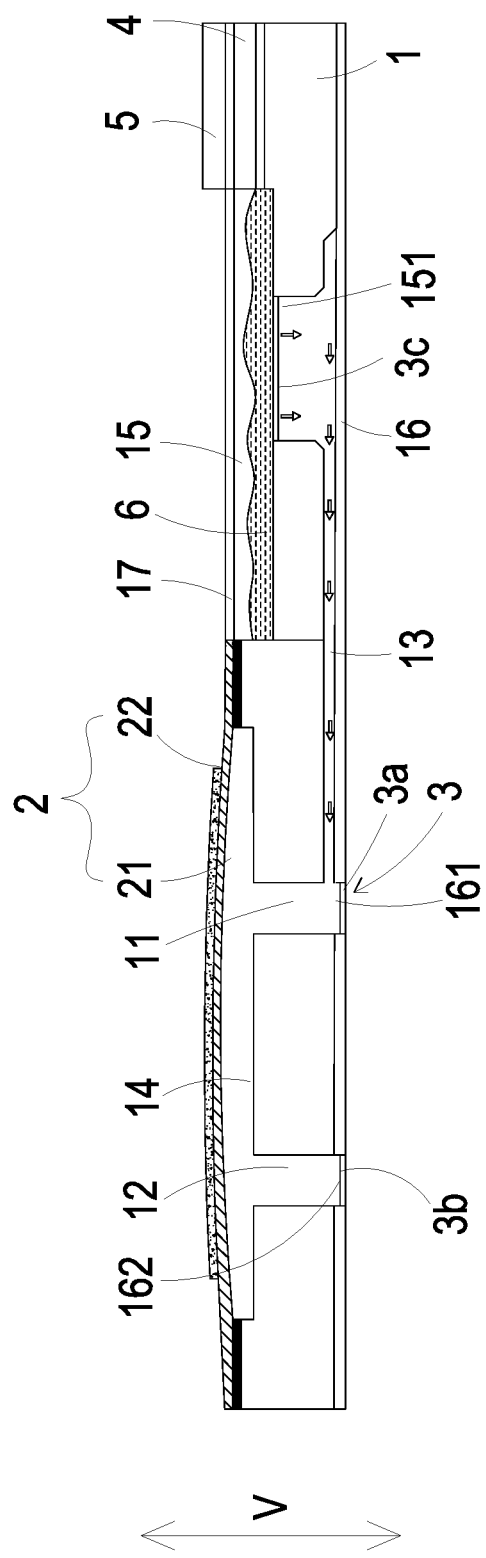
Figure 2D:
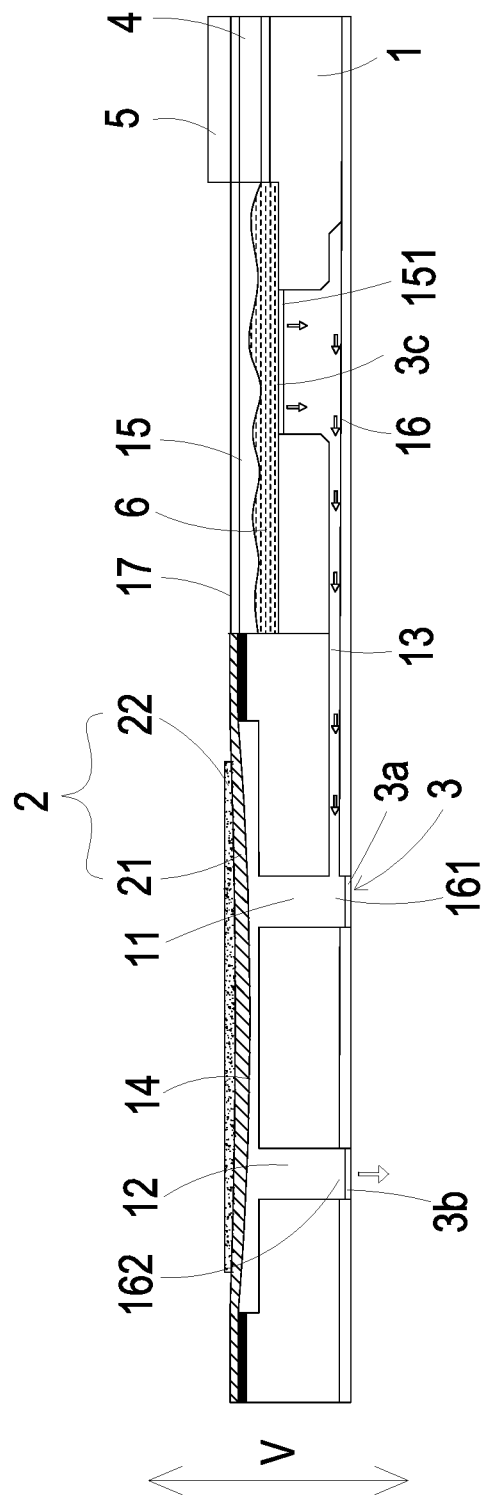

Please refer to FIGS. 2C and 2D. When the micro-monitor 5 has positioned the target blood vessel needing to be treated, the driving chip 4 controls the switching valve 3a disposed in the inlet aperture 161 to be closed, the switching valve 3b disposed in the outlet aperture 162 to be opened, and the switching valve 3c disposed in the storage outlet 151 to be opened. In this way, when the actuator 22 receives an applied voltage, the actuator 22 is activated and drives the carrier 21 to be deformed in resonance. When the carrier 21 vibrates upwardly, the volume of the compressing chamber 14 is enlarged, and thus the medicine fluid 6 is transported through the inlet channel 11 and converged in the compressing chamber 14 by the pressure gradient occurring in the compressing chamber 14. Then, when the carrier 21 vibrates downwardly, the volume of the compressing chamber 14 is reduced, and thus the medicine fluid 6 is transported through the outlet aperture 162 into the blood vessel due to the pressure gradient occurring in the compressing chamber 14. By repeating the fluid transportation actions of the micro pump as illustrated in FIGS. 2C to 2D, the actuator 22 vibrates in a vertical direction (V) in a reciprocating manner continuously, and the medicine fluid 6 is transported from the storage outlet 151 of the storage chamber 15 to the outlet aperture 162 continuously. Thus, the transportation of the medicine fluid 6 is achieved and the medicine fluid 6 is delivered to the target blood vessel needing to be treated.

Figure 3A:
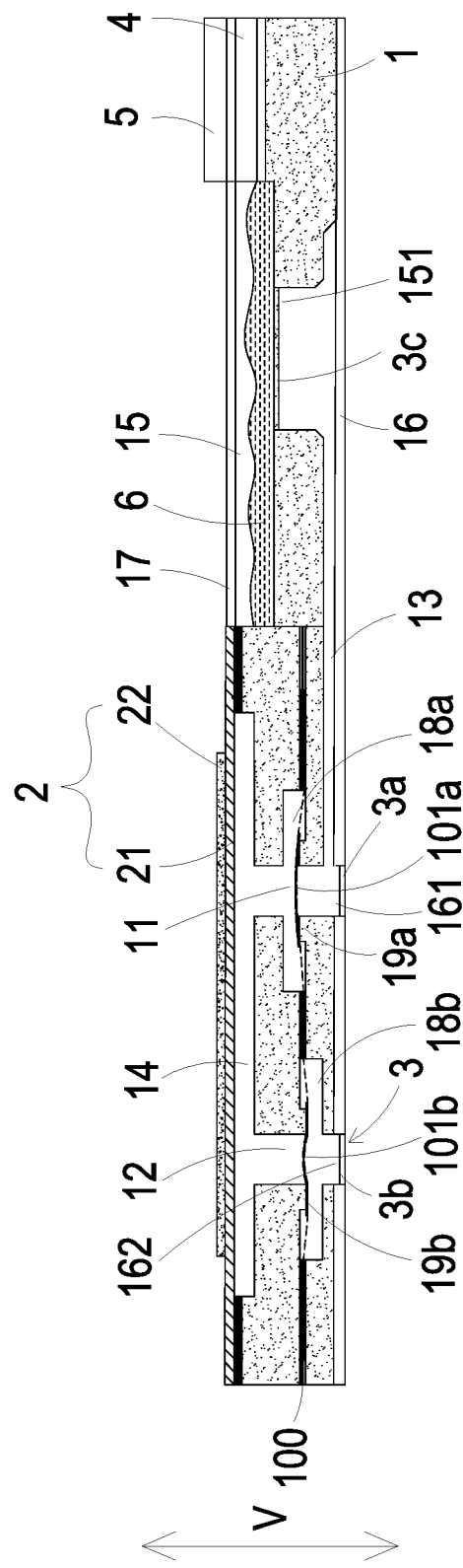
FIGS. 3A to 3C show actions of fluid in the micro pump according to a second embodiment of the present disclosure.
Figure 3B:
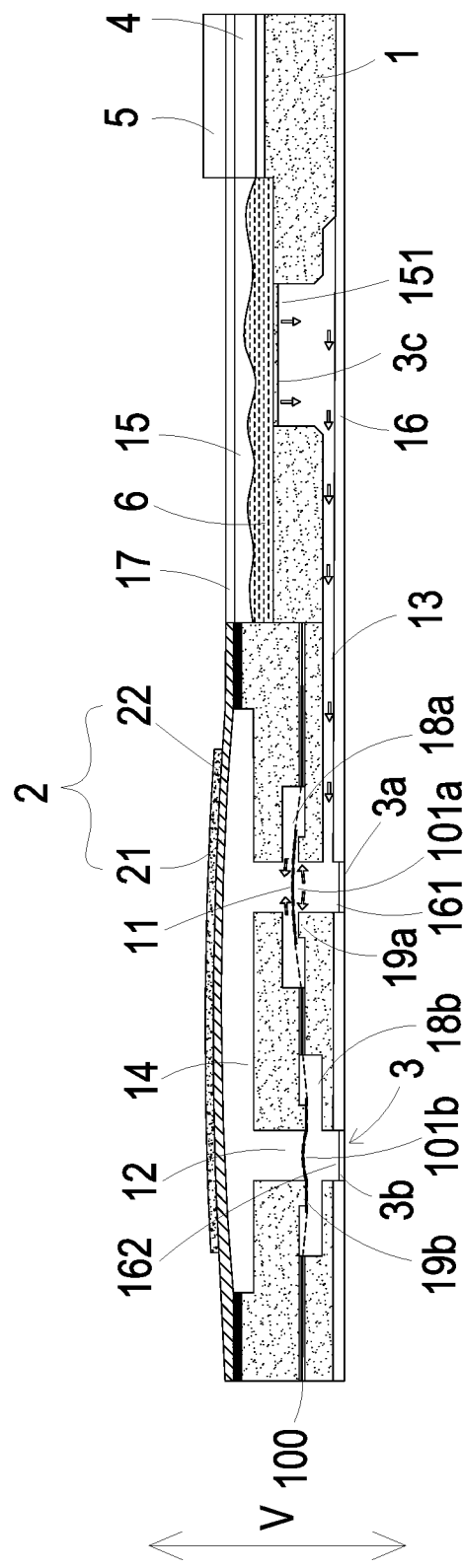
Figure 3C:
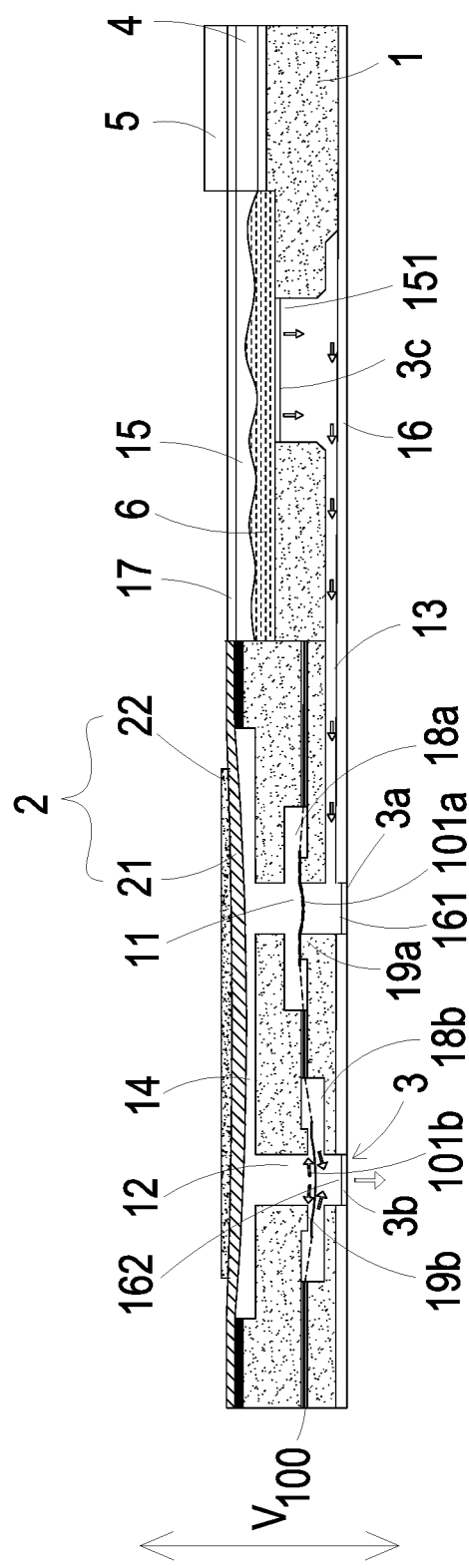
Figure 4:
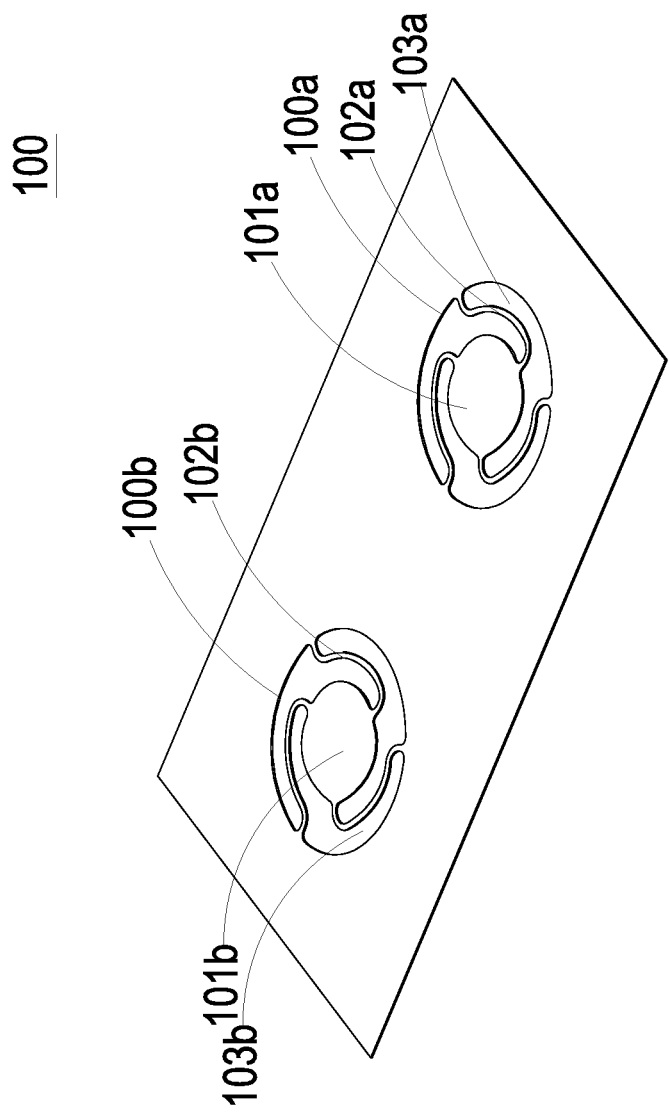
FIG. 4 is a schematic structural view illustrating the valve membrane of the micro pump according to a second embodiment of the present disclosure and taken from the front side.

Please refer to FIGS. 3A, 3B and 3C. In a second embodiment of the present disclosure, the substrate 1 further includes a first chamber 18a and a second chamber 18b disposed within the inlet channel 11 and the outlet channel 12, respectively. The substrate 1 further includes a first convex structure 19a disposed within the first chamber 18a and a second convex structure 19b disposed within the second chamber 18b. The first convex structure 19a is disposed in position corresponding to the inlet channel 11 on the bottom of the first chamber 18a. The second convex structure 19b is disposed in position corresponding to the outlet channel 12 on the top of the second chamber 18b. In this embodiment, the micro pump further includes a valve membrane 100. Referring to FIG. 4, the valve membrane 100 includes a first valve plate 101a and a second valve plate 101*b* at a first perforated region 100*a* and a second perforated region 100*b*, respectively. The first valve plate 101*a* and the second valve plate 101*b* have an identical thickness. The valve membrane 100 further includes plural first extension parts 102*a* and plural second extension parts 102*b*. The first extension parts 102*a* and the second extension parts 102*b* are arranged around the first valve plate 101*a* and the second valve plate 101*b* for elastically supporting the first valve plate 101*a* and the second valve plate 101*b*, respectively. The valve membrane 100 further includes plural first hollow parts 103*a* and plural second hollow parts 103*b*. The first hollow parts 103*a* are arranged between the first extension parts 102*a*. The second hollow parts 103*b* are arranged between the second extension parts 102*b*. When external forces are exerted on the first valve plate 101*a* and the second valve plate 101*b*, it may induce deformation and displacement of the first valve plate 101*a* and the second valve plate 101*b* since the first valve plate 101*a* and the second valve plate 101*b* are elastically supported by the first extension parts 102*a* and the second extension parts 102*b*, respectively. Therefore, the valve structure switching between open and closed states is formed, in accordance with the deformation and displacement. Preferably but not exclusively, the first valve plate 101*a* and the second valve plate 101*b* have circular shapes, rectangular shapes, square shapes or arbitrary shapes, but not limited thereto. Please refer to FIGS. 3B and 3C, again. The first valve plate 101*a* covers the inlet channel 11 and in close contact with the first convex structure 19*a* in the inlet channel 11, so that a pre-force is formed to achieve a good sealing effect on the pre-closing and to avoid reversed flow. The second valve plate 101*b* covers the outlet channel 12 and in close contact with the second convex structure 19*b* in the outlet channel 12, so that a pre-force is formed to achieve a good sealing effect on the pre-closing and to avoid reversed flow. Therefore, when the micro pump of the present disclosure is in a non-enabled state, the fluid transported between the inlet channel 11 and the outlet channel 12 of the micro pump will not be reversely returned.

Please refer to FIGS. 3B, 3C and 4. The first valve plate 101*a* and the second valve plate 101*b* of the valve membrane 100 are driven to move while the flow-guiding-and-actuating unit 2 is actuated to compress the volume of the compressing chamber 14, so as to control the inlet channel 11 and the outlet channel 12 to be in an open state or a closed state and avoid the effect of reversed flow. As shown in FIG. 3B, when the driving chip 4 controls the switching valve 3*c* disposed in the storage outlet 151 to be opened, the medicine fluid 6 is introduced into the branch channel 13 and thus transported to the inlet channel 11. When the actuator 22 is actuated to work in response to an applied voltage, the carrier 21 is driven to deform and vibrate upwardly and the volume of the compressing chamber 14 is enlarged to result in suction. In response to the suction, the first valve plate 101*a* disposed in the inlet channel 11 is rapidly separated from the contacted first convex structure 19*a* so that the first valve plate 101*a* is operated in the open state. In response to the suction, the second valve plate 101*b* corresponding to the outlet channel 12 is in close contact with the second convex structure 19*b* so that the second valve plate 101*b* is operated in the closed state. Consequently, the medicine fluid 6 is transported through the first hollow parts 103*a* within the inlet channel 11 into the first chamber 18*a* in response to the suction, and thus converged in the compressing chamber 14. Then, as shown in FIG. 3C, when the carrier 21 is driven to deform and vibrate downwardly and the volume of the compressing chamber 14 is shrunken to result in a pushing force. In response to the pushing force, the first valve plate 101*a* disposed in the inlet channel 11 is pushed back and in close contact with the first convex structure 19*a*, so that the first valve plate 101*a* is operated in the closed state, and there is no reversed flow. In response to the pushing force, the second valve plate 101*b* disposed in the outlet channel 12 is separated from the second convex structure 19*b* so that the second valve plate 101*b* is operated in the open state. Consequently, the medicine fluid 6 converged in the compressing chamber 14 is compressed and transported through the second hollows parts 103*b* within the outlet channel 12 into the second chamber 18*b*, and thus transported to the outlet aperture 162 through the outlet channel 12. By repeating the fluid transportation actions of the micro pump as illustrated in FIGS. 3B to 3C, the actuator 22 vibrates in a vertical direction (V) in a reciprocating manner continuously to work on the compressing chamber 14, and the medicine fluid 6 is transported from the storage outlet 151 of the storage chamber 15 to the outlet aperture 162 continuously. Thus, the transportation of the medicine fluid 6 is achieved and the medicine fluid 6 is delivered to the target blood vessel.

Figure 5A:
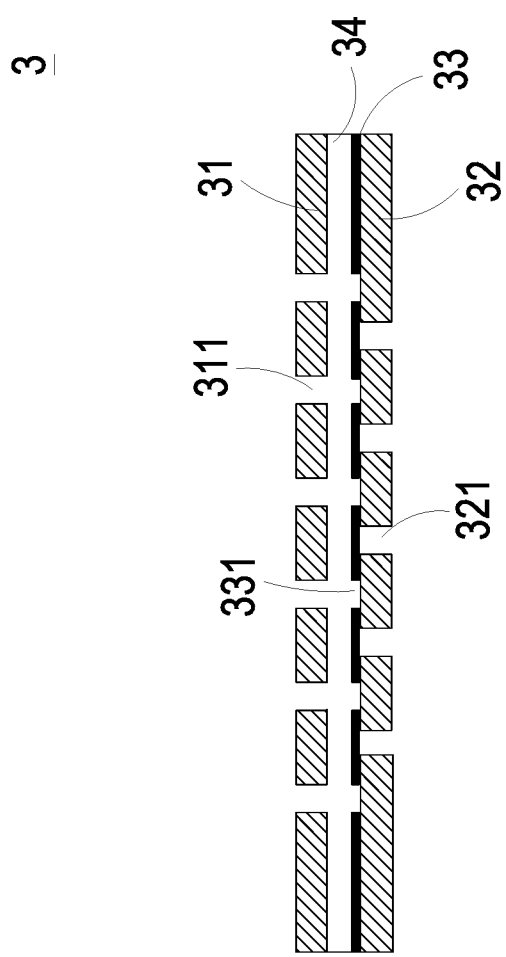
FIGS. 5A and 5B are schematic diagrams illustrating the actuations of switching valves of the micro pump of the present disclosure.
Figure 5B:
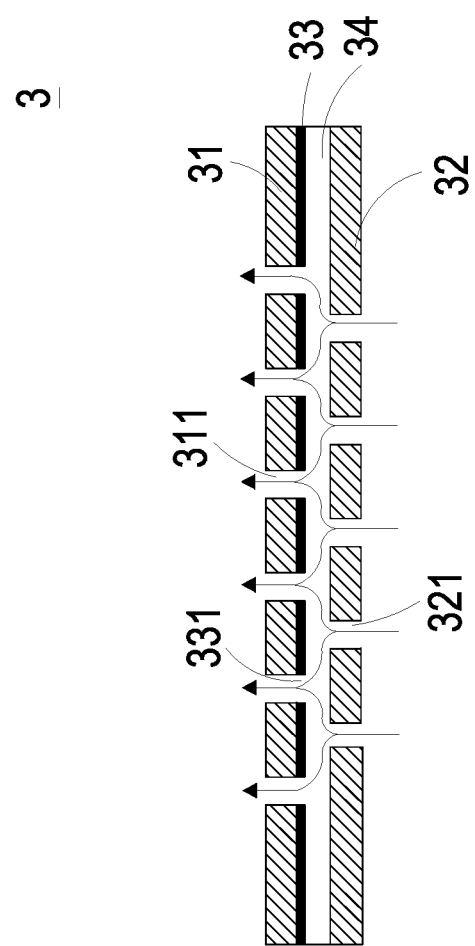

The implementation of the driving chip 4 controlling the switching valve 3 in the present disclosure is exemplified and described as follows. As shown in FIGS. 5A and 5B, a first aspect of the switching valve 3 includes a stationary component 31, a sealing component 32 and a displacement component 33. The displacement component 33 is disposed within an accommodation space 34 formed between the stationary component 31 and the sealing component 32. The stationary component 31 has at least two first orifices 311. The displacement component 33 has at least two second orifices 331 respectively corresponding in position to the at least two first orifices 311 of the stationary component 31. The sealing component 32 has at least one third orifice 321. The at least one third orifice 321 of the sealing component 32 is misaligned with the at least two first orifices 311 of the stationary component 31 and the at least two second orifices 331 of the displacement component 33. When the fluid is transported in a direction indicated by arrows in FIG. 5B, the displacement component 33 is pushed to move upwardly toward the stationary component 31. As a result, the displacement component 33 comes into contact with the stationary component 31 so as to open the third orifices 321 of the sealing component 32 at the same time, and the fluid is inhaled through the third orifices 321 of the sealing component 32. Since the second orifices 331 of the displacement component 33 are aligned with the first orifices 311 of the stationary component 31, respectively, the second orifices 331 and the first orifices 311 are in communication with each other. The switching valve 3 is thus opened.

In a second aspect of the switching valve 3 in the present disclosure, the displacement component 33 is made of a charged material, and the stationary component 31 is made of a bipolar conductive material. The stationary component 31 is electrically connected to a driving chip 4, so that the change electrical polarity (positive polarity or negative polarity) of the stationary component 31 can be controlled by the driving chip 4. In case that the displacement component 33 is made of a negative charged material, while the switching valve 3 is required to be opened, the stationary component 31 is in positive polarity in response to the control of the driving chip 4. Since the displacement component 33 and the stationary component 31 are maintained in reversed polarities, the displacement component 33 moves toward the stationary component 31 to open the switching valve 3 (as shown in FIG. 5B). In contrast, in case that the displacement component 33 is made of the negative charged material, while the switching valve 3 is required to be closed, the stationary component 31 is in negative polarity in response to the control of the driving chip 4. Since the displacement component 33 and the stationary component 31 are maintained in identical polarities, the displacement component 33 moves toward the sealing component 32 to close the switching valve 3 (as shown in FIG. 5A).

In a third aspect of the switching valve 3 in the present disclosure, the displacement component 33 is made of a magnetic material, and the stationary component 31 is made of an electromagnet material and can be controlled to change the electrical polarity. The stationary component 31 is electrically connected to the driving chip 4, so that the electrical polarity (positive polarity or negative polarity) of the stationary component 31 is controlled by the driving chip 4. In case that the displacement component 33 is made of a negative-magnetic material, while the switching valve 3 is required to be opened, the stationary component 31 is in positive polarity in response to the control of the driving chip 4. Since the displacement component 33 and the stationary component 31 are maintained in reversed polarities, the displacement component 33 moves toward the stationary component 31 to open the switching valve 3 (as shown in FIG. 5B). In contrast, in case that the displacement component 33 is made of a negative-magnetic material, while the switching valve 3 is required to be closed, the stationary component 31 is in negative polarity in response to the control of the driving chip 4. Since the displacement component 33 and the stationary component 31 are maintained in identical polarities, the displacement component 33 moves toward the sealing component 32 to close the switching valve 3 (as shown in FIG. 5A).

In summary, the present disclosure provides a micro pump, which is implanted in the human blood vessel and receives the external command through a communication connector of the driving chip. The driving chip enables the flow-guiding-and-actuating unit and the micro-monitor. Simultaneously, the switching valves are controlled to open or close by the driving chip. Thus, a flow of the fluid is formed and the kinetic energy that the flow of the fluid possessed facilitates displacement of the micro pump in the blood vessel. In addition, by controlling the open/closed states of the switching valves disposed in the inlet aperture, the outlet aperture, the storage outlet to be opened or closed, and by the actuation of the flow-guiding-and- actuating unit, the medicine fluid stored in the storage chamber is transported to the outlet aperture and delivered to the target blood vessel needing to be treated. Thus, the transportation of the medicine fluid is achieved. Moreover, since the micro pump of the present disclosure can be implanted in human blood vessel, it can detect the patient's body condition at anytime and anywhere, and immediately deliver the therapeutic drug. It benefits of high efficiency and flexible utilization.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A micro pump for being implanted into a human blood vessel, comprising:

a substrate comprising a plurality of guiding channels, a compressing chamber, a storage chamber, a first covering component and a second covering component, wherein the plurality of guiding channels comprises an inlet channel, an outlet channel and a branch channel in communication with the inlet channel, the first covering component covers the inlet channel, the outlet channel and the branch channel and includes an inlet aperture corresponding to the inlet channel and an outlet aperture corresponding to the outlet channel, the compressing chamber is in communication with the inlet channel and the outlet channel, the second covering component covers the storage chamber so as to store a medicine fluid in the storage chamber, and the storage chamber has a storage outlet in communication with the branch channel;

a flow-guiding-and-actuating unit configured to cover the compressing chamber, wherein when the flow-guiding-and-actuating unit is powered, the flow-guiding-and-actuating unit is enabled to change the volume of the compressing chamber so as to transport fluid;

a plurality of switching valves covering the inlet aperture, the outlet aperture and the storage outlet, respectively;

a driving chip packaged on the substrate in a system-in-package manner, the driving chip powering and enabling the flow-guiding-and-actuating unit, and controlling open/closed states of the plurality of switching valves, wherein the driving chip includes a communication connector; and a micro-monitor packaged on the substrate in the system-in-package manner, the micro-mirror being controlled by the driving chip to be enabled;

wherein the micro pump is configured to be implanted in the human blood vessel and receives an external command through the communication connector of the driving chip to enable the flow-guiding-and-actuating unit and the micro-monitor, and to control the open/closed states of the switching valves covering the inlet aperture and the outlet aperture, so that a fluid flow is generated and kinetic energy that the fluid flow possesses facilitates displacement of the micro pump in the human blood vessel, wherein the micro-monitor is enabled to monitor a target blood vessel needing to be treated, wherein while the switching valve covering the inlet aperture is closed and the switching valves covering the outlet aperture and the storage outlet are opened, the medicine fluid stored in the storage chamber is driven by the flow-guiding-and-actuating unit to be transported to the outlet aperture and delivered to the target blood vessel.

2. The micro pump according to claim 1, wherein the flow-guiding-and-actuating unit comprises a carrier and an actuator, the carrier covers the compressing chamber, and the actuator is attached to a surface of the carrier, wherein in response to an applied voltage, the actuator drives the carrier to be deformed in resonance so as to drive the fluid between the inlet channel and the outlet channel to be transported.

3. The micro pump according to claim 2, wherein the actuator is a piezoelectric component.

4. The micro pump according to claim 1, further comprising a valve membrane disposed in the inlet channel and the outlet channel for controlling the inlet channel and the outlet channel to be in an open state or a closed state while the flow-guiding-and-actuating unit is enabled to change the volume of the compressing chamber.

5. The micro pump according to claim 4, wherein the substrate further comprises convex structures in the inlet channel and the outlet channel to provide a pre-force when the valve membrane is abutting against the convex structures.

6. The micro pump according to claim 1, wherein the driving chip comprises a graphene battery for providing power.

7. The micro pump according to claim 1, wherein the communication connector transmits and receives information via a wireless communication path.

8. The micro pump according to claim 1, wherein each of the plurality of switching valves comprises a stationary component, a sealing component and a displacement component, the displacement component is disposed between the stationary component and the sealing component, the stationary component has at least two first orifices, and the displacement component has at least two second orifices respectively corresponding in position to the at least two first orifices; and the sealing component has at least one third orifice misaligned with the at least two first orifices and the at least two second orifices.

9. The micro pump according to claim 8, wherein the displacement component is made of a charged material, and the stationary component is made of a bipolar conductive material, wherein the displacement component and the stationary component are maintained in reversed polarities, the displacement component moves close to the stationary component so as to open the switching valve.

10. The micro pump according to claim 9, wherein the polarity of the stationary component is controlled by the driving chip.

11. The micro pump according to claim 8, wherein the displacement component is made of a charged material, and the stationary component is made of a bipolar conductive material, wherein the displacement component and the stationary component are maintained in identical polarities, the displacement component moves close to the stationary component so as to close the switching valve.

12. The micro pump according to claim 11, wherein the polarity of the stationary component is controlled by the driving chip.

13. The micro pump according to claim 8, wherein the displacement component is made of a magnetic material, and the stationary component is made of an electromagnet material, wherein the displacement component and the stationary component are maintained in reversed polarities, the displacement component moves close to the stationary component so as to open the switching valve.

14. The micro pump according to claim 13, wherein the polarity of the stationary component is controlled by the driving chip.

15. The micro pump according to claim 8, wherein the displacement component is made of a magnetic material, and the stationary component is made of an electromagnet material, wherein the displacement component and the stationary component are maintained in identical polarities, the displacement component moves close to the sealing component so as to close the switching valve.

16. The micro pump according to claim 15, wherein the polarity of the stationary component is controlled by the driving chip.

17. A micro pump for being implanted into a human blood vessel, comprising:
at least one substrate comprising a plurality of guiding channels, at least one compressing chamber, at least one storage chamber, at least one first covering component and at least one second covering component, wherein the plurality of guiding channels comprises at least one inlet channel, at least one outlet channel and at least one branch channel in communication with the inlet channel, the first covering component covers the inlet channel, the outlet channel and the branch channel and includes at least one inlet aperture corresponding to the inlet channel and at least one outlet aperture corresponding to the outlet channel, the compressing chamber is in communication with the inlet channel and the outlet channel, the second covering component covers the storage chamber so as to store at least one medicine fluid in the storage chamber, and the storage chamber has at least one storage outlet in communication with the branch channel;
at least one flow-guiding-and-actuating unit and configured to cover the compressing chamber, wherein when the flow-guiding-and-actuating unit is powered, the flow-guiding-and-actuating unit is enabled to change the volume of the compressing chamber so as to transport fluid;
a plurality of switching valves covering the inlet aperture, the outlet aperture and the storage outlet, respectively;
at least one driving chip packaged on the substrate in a system-in-package manner, the driving chip powering and enabling the flow-guiding-and-actuating unit, and controlling open/closed states of the plurality of switching valves, wherein the driving chip includes at least one communication connector; and
at least one micro-monitor packaged on the substrate in the system-in-package manner, the micro-monitor being controlled by the driving chip to be enabled;
wherein the micro pump is configured to be implanted in the human blood vessel and receives at least one external command through the communication connector of the driving chip to enable the flow-guiding-and-actuating unit and the micro-monitor, and to control the open/closed states of the switching valves covering the inlet aperture and the outlet aperture, so that a fluid flow is generated and kinetic energy that the fluid flow possesses facilitates displacement of the micro pump in the human blood vessel, wherein the micro-monitor is enabled to monitor a target blood vessel needing to be treated, wherein while the switching valve covering the inlet aperture is closed and the switching valves covering the outlet aperture and the storage outlet are opened, the medicine fluid stored in the storage chamber is driven by the flow-guiding-and-actuating unit to be transported to the outlet aperture and delivered to the target blood vessel.

* * * * *